(12) United States Patent
Rizoiu et al.

(10) Patent No.: US 6,254,597 B1
(45) Date of Patent: Jul. 3, 2001

(54) TISSUE REMOVER AND METHOD

(75) Inventors: Ioana M. Rizoiu, Dana Point; Andrew I. Kimmel, San Clemente, both of CA (US)

(73) Assignee: BioLase Technology, Inc., San Clemente, CA (US)

( * ) Notice: Subject to any disclaimer, the term of this patent is extended or adjusted under 35 U.S.C. 154(b) by 0 days.

(21) Appl. No.: 09/188,072

(22) Filed: Nov. 6, 1998

Related U.S. Application Data

(63) Continuation-in-part of application No. 08/985,513, filed on Dec. 5, 1997, which is a continuation of application No. 08/522,503, filed on Aug. 31, 1995, now Pat. No. 5,741,247, and a continuation-in-part of application No. 08/995,241, filed on Dec. 17, 1997, which is a continuation of application No. 08/575,775, filed on Dec. 20, 1995, now Pat. No. 5,785,521.

(60) Provisional application No. 60/064,465, filed on Nov. 6, 1997.

(51) Int. Cl.⁷ .................................................. A61B 18/18
(52) U.S. Cl. ................................ 606/13; 604/35; 606/10; 607/89
(58) Field of Search .................... 604/19, 27, 28, 604/35, 542; 606/3, 15, 19, 45, 10, 9, 13; 607/88, 89

(56) References Cited

U.S. PATENT DOCUMENTS

| | | | | |
|---|---|---|---|---|
| 4,931,047 | * | 6/1990 | Broadwin et al. | 606/45 |
| 4,985,027 | * | 1/1991 | Dressel | 606/15 |
| 5,263,950 | * | 11/1993 | L'Esperance, Jr. | 606/6 |
| 5,741,247 | * | 4/1998 | Rizoiu et al. | 606/10 |
| 5,785,521 | * | 7/1998 | Rizoiu et al. | 433/29 |

* cited by examiner

*Primary Examiner*—Michael Peffley
*Assistant Examiner*—Nick Guy
(74) *Attorney, Agent, or Firm*—Stout, Uxa, Buyan & Mullins, LLP

(57) ABSTRACT

An electromagnetically induced cutting mechanism provides accurate cutting operations on soft tissues. The electromagnetically induced cutter is adapted to interact with atomized fluid particles. A non-thermal tissue remover comprises an aspiration cannula housing a fluid and energy guide for conducting electromagnetically induced mechanical cutting forces to the site within a patient's body for aspiration of soft tissue. The cannula is provided with an aspiration inlet port adjacent the cannula distal end. The proximal end of the cannula is provided with fluid flow connection to an aspiration source. Separated soft tissue and fluid are aspirated through the aspiration inlet port and the cannula by an aspiration source at the proximal end of the cannula.

14 Claims, 7 Drawing Sheets

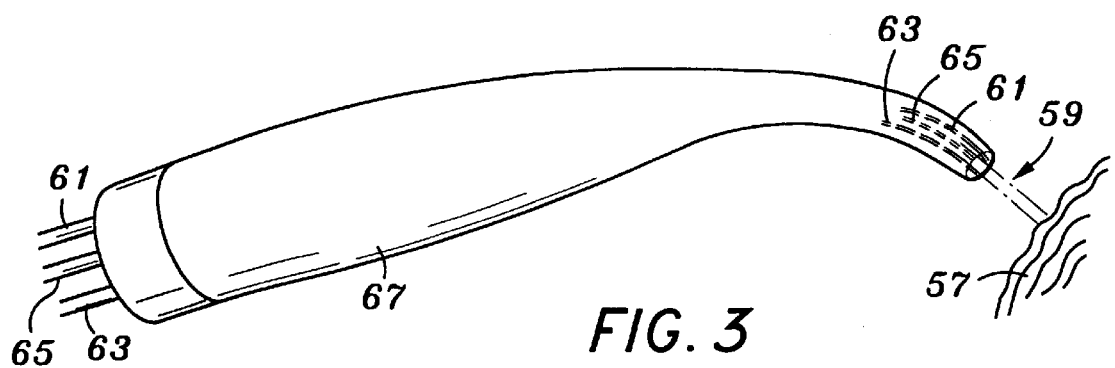
FIG. 3
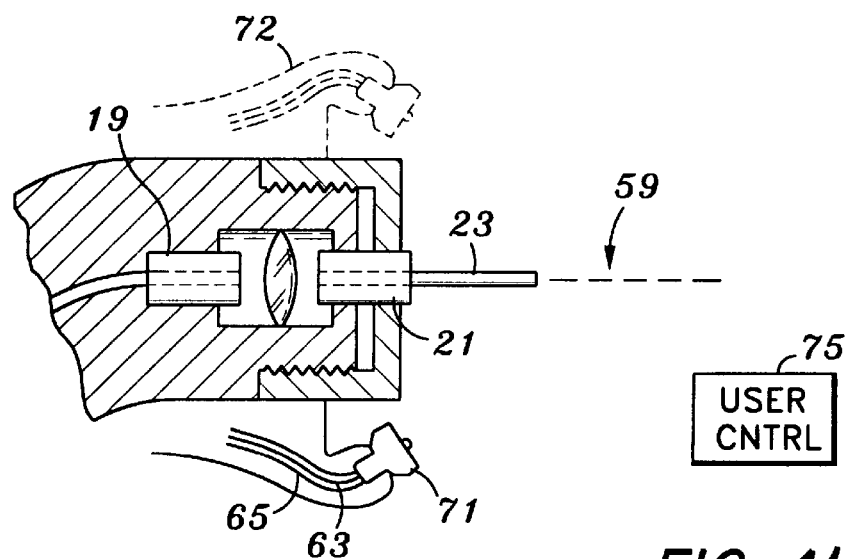
FIG. 4a
FIG. 4b
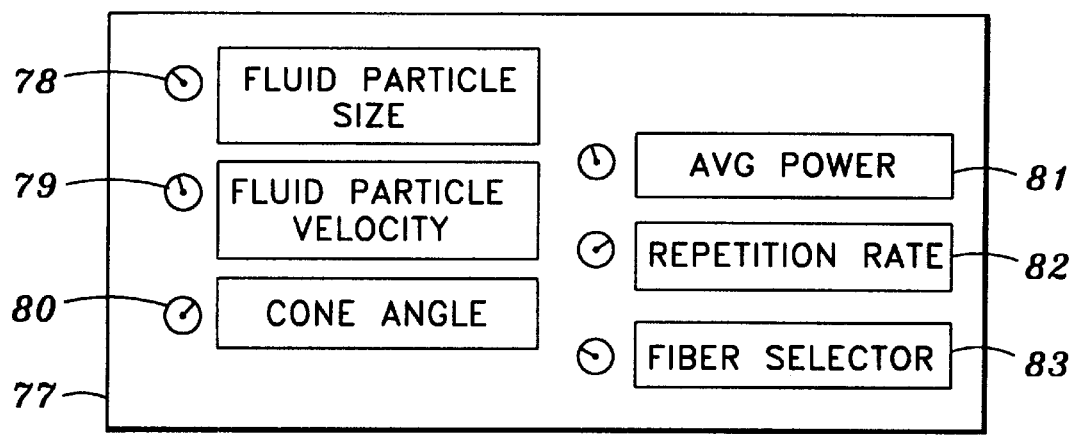
FIG. 5

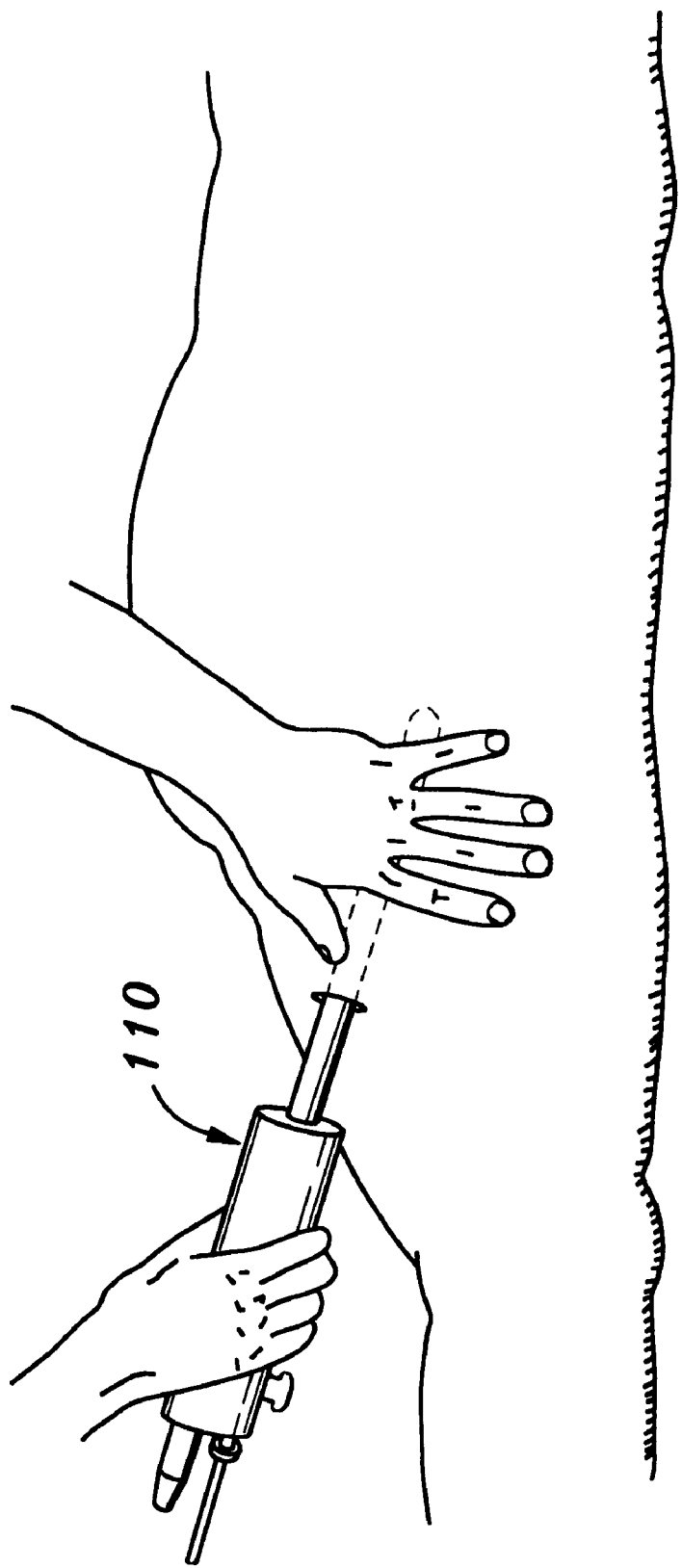

TISSUE REMOVER AND METHOD

PRIORITY INFORMATION

This application claims the benefit of U.S. Provisional Applicaion No. 60/064,465 filed on Nov. 6, 1997 and entitled ELECTROMAGNETICALLY INDUCED MECHANICAL CUTTER FOR LYPOSUCTION the contents of which are expressly incorporated herein by reference. This application is a continution-in-part of co-pending U.S. application Ser. No. 08/985,513 filed on Dec. 5, 1997 and entitled USER PROGRAMMABLE COMBINATION OF ATOMIZED PARTICLES FOR ELECTROMAGNETICALLY INDUCED CUTTING, which is a continuation of U.S. application Ser. No. 08/522,503 filed on Aug. 31, 1995 and entitled USER PROGRAMMABLE COMBINATION OF ATOMIZED PARTICLES FOR ELECTROMAGNETICALLY INDUCED CUTTING which issued into U.S. Pat. No. 5,741,247, both of which are commonly assigned and the contents of which are expressly incorporated herein by reference. This appication is also a continuation-in-part of co-pending U.S. application Ser. No. 08/995,241 filed on Dec. 17, 1997 and entitled FLUID CONDITIONING SYSTEM, which is a continuation of U.S. application Ser. No. 08/575,775, filed on Dec. 20, 1995 and entitled FLUID CONDITIONING SYSTEM which issued into U.S. Pat. No. 5,785,521, both of which are commonly assigned and the contents of which are expressly incorporated herein by reference.

BACKGROUND OF THE INVENTION

1. Field of the Invention

The present invention relates generally to medical apparatus and, more particularly, to methods and apparatus for cutting and removing soft tissue by aspiration.

2. Description of Related Art

Turning to FIG. 1, a prior art optical cutter includes a fiber guide tube 5, a water line 7, an air line 9, and an air knife line 11 for supplying pressurized air. A cap 15 fits onto the hand-held apparatus 13 and is secured via threads 17. The fiber guide tube 5 abuts within a cylindrical metal piece 19. Another cylindrical metal piece 21 is a part of the cap 15. The pressurized air from the air knife line 11 surrounds and cools the laser as the laser bridges the gap between the two metal cylindrical objects 19 and 21. Air from the air knife line 11 flows out of the two exhausts 25 and 27 after cooling the interface between elements 19 and 21.

The laser energy exits from the fiber guide tube 23 and is applied to a target surface of the patient. Water from the water line 7 and pressurized air from the air line 9 are forced into the mixing chamber 29. The air and water mixture is very turbulent in the mixing chamber 29, and exits this chamber through a mesh screen with small holes 31. The air and water mixture travels along the outside of the fiber guide tube 23, and then leaves the tube and contacts the area of surgery.

Other prior art devices include optical cutting systems utilizing the expansion of water to destroy and remove tooth material, such as disclosed in U.S. Pat. No. 5,199,870 to Steiner et al. This prior art approach requires a film of liquid having a thickness of between 10 and 200 µm. U.S. Pat. No. 5,267,856 to Wolbarsht et al. discloses a cutting apparatus that requires water to be inserted into pores of a material and then irradiated with laser energy. In both patents the precision and accuracy of the cut is highly dependent upon the precision and accuracy of the water film on the material or the water within the pores.

Devices have existed in the prior art for utilizing laser energy to perform liposuction and body contouring procedures, wherein laser energy facilites the separating of soft tissue from a patient in vivo. U.S. Pat. No. 4,985,027 to Dressel discloses a tissue remover that utilizes laser energy from a Nd:YAG to separate tissue held within a cannula, the contents of which are expressly incorporated herein by reference. Use of the Nd:YAG laser for in vivo tissue removal is in some ways inefficient, since the energy from the Nd:YAG laser is not highly absorbed by water. Further, the Nd:YAG laser and other lasers, such as an Er:YAG laser, use thermal heating as the cutting mechanism. Adjacent tissue can be charred or thermally damaged and, further, noxious and potentially toxic smoke can be generated during the thermal cutting operations performed by these prior-art devices.

SUMMARY OF THE INVENTION

The present invention discloses an electromagnetically induced mechanical cutting mechanism, which can provide accurate cutting operations on hard and soft tissues, and other materials as well. Soft tissues may include fat, skin, mucosa, gingiva, muscle, heart, liver, kidney, brain, eye, and vessels, and hard tissue may include tooth enamel, tooth dentin, tooth cementum, tooth decay, amalgam, coposites materials, tarter and calculus, bone and cartilage.

The electromagnetically induced cutter is capable of providing extremely fine and smooth incisions, irrespective of the cutting surface. Additionally, a user programmable combination of atomized particles allows for user control of various cutting parameters. The various cutting parameters may also be controlled by changing spray nozzles and electromagnetic energy source parameters. Applications for the present invention include medical, such as liposuction and dental, and other environments where an objective is to precisely remove surface materials without inducing thermal damage, uncontrolled cutting parameters, and/or rough surfaces inappropriate for ideal bonding. The present invention further does not require any films of water or any particularly porous surfaces to obtain very accurate and controlled cutting. Since thermal heating is not used as the cutting mechanism, thermal damage does not occur. Adjacent tissue is not charred or thermally damaged and, further, noxious and potentially toxic smoke is attenuated or completely eliminated.

The electromagnetically induced mechanical cutter of the present invention includes an electromagnetic energy source, which focuses electromagnetic energy into a volume of air adjacent to a target surface. The target surface may comprise fatty tissue within a cannula, for example. A user input device specifies a type of cut to be performed, and an atomizer responsive to the user input device places a combination of atomized fluid particles into the volume of air. The electromagnetic energy is focused into the volume of air, and the wavelength of the electromagnetic energy is selected to be substantially absorbed by the atomized fluid particles in the volume of air. Upon absorption of the electromagnetic energy the atomized fluid particles expand and impart mechanical cutting forces onto the target surface.

The invention, together with additional features and advantages thereof may best be understood by reference to the following description taken in connection with the accompanying illustrative drawings.

BRIEF DESCRIPTION OF THE DRAWINGS

FIG. 3 illustrates one embodiment of the electromagnetically induced mechanical cutter of the present invention;

FIGS. 4a and 4b illustrate a preferred embodiment of the electromagnetically induced mechanical cutter;

FIG. 5 illustrates a control panel for programming the combination of atomized fluid particles according to the present invention;

FIG. 14 is a cut-away detail of the laser soft tissue device of the present invention illustrated in position for performing liposuction within a fatty deposit of a body intermediate overlying epidermal layer and underlying muscle layer.

DESCRIPTION OF THE PRESENTLY PREFERRED EMBODIMENTS

Figure 2:
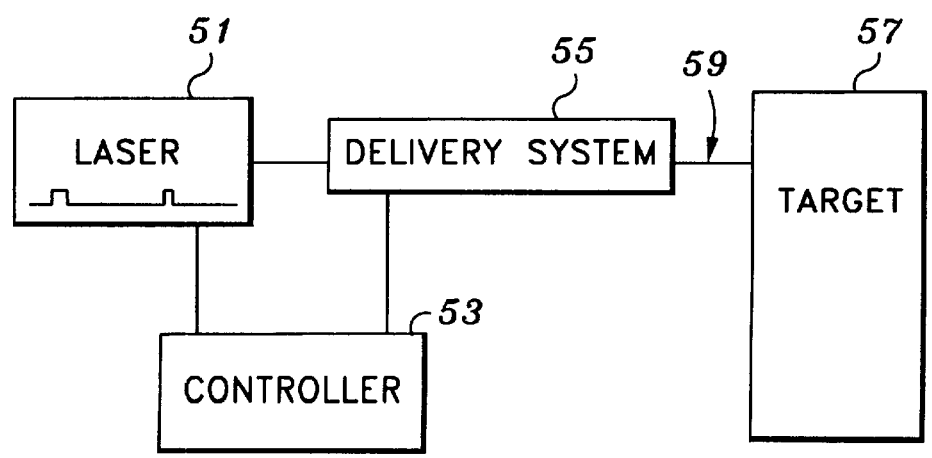
FIG. 2 is a schematic block diagram illustrating the electromagnetically induced mechanical cutter of the present invention.

FIG. 2 is a block diagram illustrating an electromagnetically induced mechanical cutter in accordance with the present invention. An electromagnetic energy source 51 is coupled to both a controller 53 and a delivery system 55. The delivery system 55 imparts mechanical forces onto the target surface 57. As presently embodied, the delivery system 55 comprises a fiber optic guide for routing the laser 51 into an interaction zone 59, located above the target surface 57. The delivery system 55 further comprises an atomizer for delivering user-specified combinations of atomized fluid particles into the interaction zone 59. The controller 53 controls various operating parameters of the laser 51, and further controls specific characteristics of the user-specified combination of atomized fluid particles output from the delivery system 55.

FIG. 3 shows a simple embodiment of the electromagnetically induced mechanical cutter of the present invention, in which a fiber optic guide 61, an air tube 63, and a water tube 65 are placed within a hand-held housing 67. The water tube 65 is operated under a relatively low pressure, and the air tube 63 is operate under a relatively high pressure. The laser energy from the fiber optic guide 61 focuses onto a combination of air and water, from the air tube 63 and the water tube 65, at the interaction zone 59. Atomized fluid particles in the air and water mixture absorb energy from the laser energy of the fiber optic tube 61, and explode. The explosive forces from these atomized fluid particles impart mechanical cutting forces onto the target surface 57.

Figure 1:
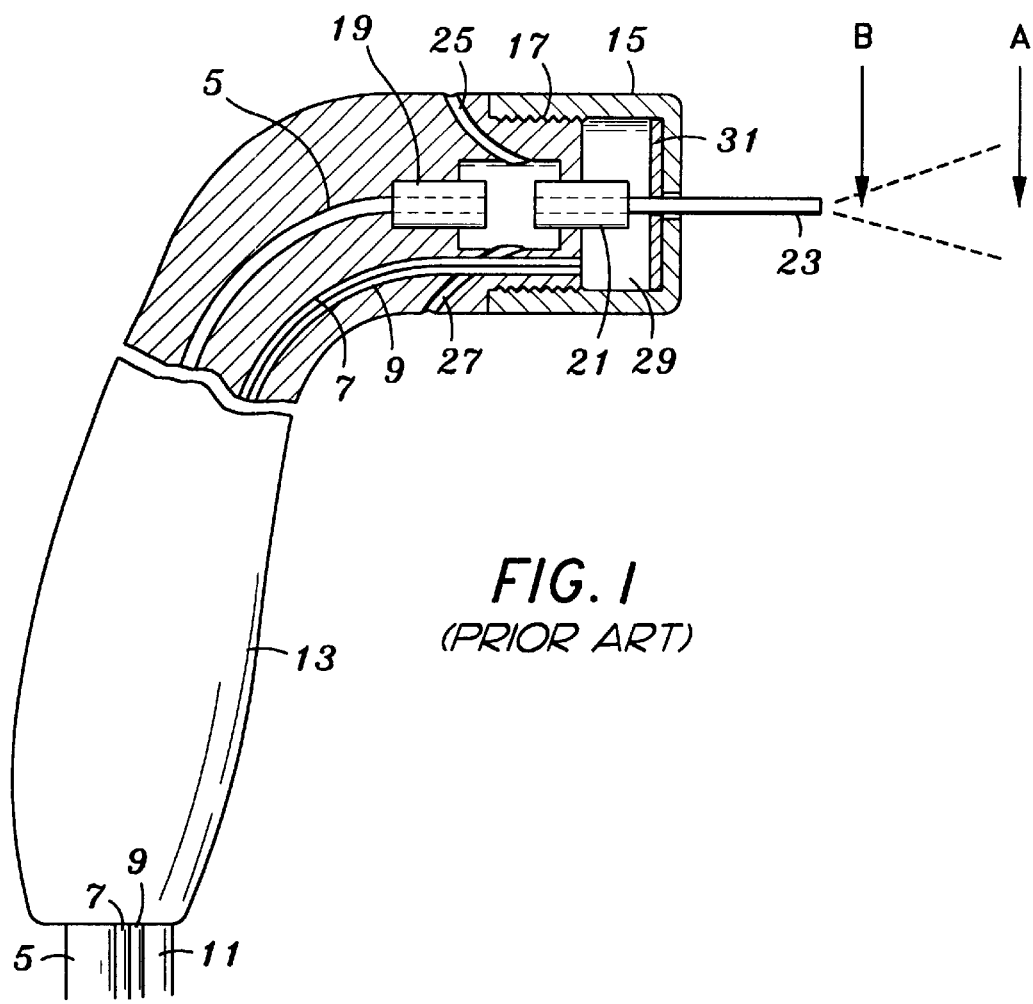
FIG. 1 is a conventional optical cutter apparatus.

Turning back to FIG. 1, the prior art optical cutter focuses laser energy onto a target surface at an area A, for example, and the electromagnetically induced mechanical cutter of the present invention focuses laser energy into an interaction zone B, for example. The prior art optical cutter uses the laser energy directly to cut tissue, and the electromagnetically induced mechanical cutter of the present invention uses the laser energy to expand atomized fluid particles to thus impart mechanic cutting forces onto the target surface. The prior art optical cutter must use a large amount of laser energy to cut the area of interest, and also must use a large amount of water to both cool this area of interest and remove cut tissue.

In contrast, the electromagnetically induced mechanical cutter of the reprsent invention uses a relatively small amount of water and, further, uses only small amount of laser energy to expand atomized fluid particles generated from the water. According to the electromagnetically induced mechanical cutter of the present invention, water is not needed to cool the area of surgery, since the exploded at atomized fluid particles are cooled by exothermic reactions before they contact the target surface. Thus, atomized fluid particles of the present invention are heated, expanded, and cooled before contacting the target surface. The electromagnetically induced mechanical cutter of the present invention is thus capable of cutting without charring or discoloration.

FIG. 4a illustrates the presently preferred embodiment of the electromagnetically induced mechanical cutter. The atomizer for generating atomized fluid particles comprises a nozzle 71, which may be interchanged with other nozzles (not shown) for obtaining various spatial distributions of the atomized fluid particles, according to the type of cut desired. A second nozzle 72, shown in phantom lines, may also be used. The cutting power of the electromagnetically induced mechanical cutter is further controlled by a user control 75 (FIG. 4b). In a simple embodiment, the user control 75 controls the air and water pressure entering into the nozzle 71. The nozzle 71 is thus capable of generating many different user-specified combinations of atomized fluid particles and aerosolized sprays.

Intense energy is emitted from the fiber optic guide 23. This intense energy is preferably generated from a coherent source, such as a laser. In the presently preferred embodiment, the laser comprises either an erbium, chromium, yttrium, scandium, gallium garnet (Er, Cr:YSGG) solid state laser, which generates electromagnetic energy having a wavelength in a range of 2.70 to 2.80 microns, or an erbium, yttrium, aluminum garnet (Er:YAG) solid state laser, which generates electromagnetic energy having a wavelength of 2.94 microns. As presently preferred, the Er, Cr:YSGG solid state laser has a wavelength of approximately 2.78 microns and the Er:YAG solid state laser has a wavelength of approximately 2.94 microns.

Although the fluid emitted from the nozzle 71 preferably comprise water, other fluids may be used and appropriate wavelengths of the electromagnetic energy source may be selected to allow for high absorption by the fluid. Other possible laser systems include an erbium, yttrium, scandium, gallium garnet (Er:YSGG) solid state laser, which generates electromagnetic energy having a wavelength in a range of 2.70 to 2.80 microns; an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YALO3) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometer; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide ($CO_2$), which generates electromagnetic energy having a wavelength in a range of 9.0 to 10.6 microns. Water is chosen as the preferred fluid because of its biocompatibility, abundance, and low cost. The actual fluid used may vary as long as it is properly matched (meaning it is highly absorbed) to the selected electromagnetic energy source (i.e. laser) wavelength.

The electromagnetic energy source can be configured with the repetition rate greater than 1 Hz, the pulse duration range between 1 picosecond and 1000 microseconds, and the energy greater than 1 milliJoule per pulse. According to one operating mode of the present invention, the electromagnetic energy source has a wavelength of approximately 2.78 microns, a repetition rate of 20 Hz, a pulse duration of 140 microseconds, and an energy between 1 and 300 milliJoules per pulse.

In one preferred embodiment the electromagnetic energy source has a pulse duration on the order of nanoseconds, which is obtained by Q-switching the electromagnetic energy source, and in another preferred embodiment the electromagnetic energy source has a pulse duration on the order of picoseconds, which is obtained by mode locking the electromagnetic energy source. Q-switching is a conventional mode of laser operation which is extensively employed for the generation of high pulse power. The textbook, Solid-State Laser Engineering, Fourth Extensively Revised and Updated Edition, by Walter Koechner and published in 1996, the entire contents of which are expressly incorporated herein by reference, discloses Q-switching laser theory and various Q-switching devices. Q-switching devices generally inhibit laser action during the pump cycle by either blocking the light path, causing a mirror misalignment, or reducing the reflectivity of one of the resonator mirrors. Near the end of the flashlamp pulse, when maximum energy has been stored in the laser rod, a high Q-condition is established and a giant pulse is emitted from the laser. Very fast electronically controlled optical shutters can be made by using the electro-optic effect in crystals or liquids. An acousto-optic Q-switch launches an ultrasonic wave into a block of transparent optical material, usually fused silica. Chapter eight of the textbook, Solid-State Laser Engineering, Fourth Extensively Revised and Updated Edition, discloses the above-mentioned and other various Q-switching devices. Mode locking is a conventional procedure which phase-locks the longitudinal modes of the laser and which uses a pulse width that is inversely related to the bandwidth of the laser emission. Mode locking is discussed on pages 500–561 of the above-mentioned textbook entitled, Solid-State Laser Engineering, Fourth Extensively Revised and Updated Edition.

The atomized fluid particles provide the mechanical cutting forces when they absorb the electromagnetic energy within the interaction zone. These atomized fluid particles, however, provide a second function of cleaning and cooling the fiber optic guide from which the electromagnetic energy is output. The delivery system 55 (FIG. 2) for delivering the electromagnetic energy includes a fiber optic energy guide or equivalent which attaches to the laser system and travels to the desired work site. Fiber optics or waveguides are typically long, thin and lightweight, and are easily manipulated. Fiber optics can be made of calcium fluoride (CaF), calcium oxide (CaO2), zirconium oxide (ZrO2), zirconium fluoride (ZrF), sapphire, hollow waveguide, liquid core, TeX glass, quartz silica, germanium sulfide, arsenic sulfide, germanium oxide (GeO2), and other materials. Other delivery systems include devices comprising mirrors, lenses and other optical components where the energy travels through a cavity, is directed by various mirrors, and is focused onto the targeted cutting site with specific lenses. The preferred embodiment of light delivery for medical applications of the present invention is through a fiber optic conductor, because of its light weight, lower cost, and ability to be packaged inside of a handpiece of familiar size and weight to the surgeon, dentist, or clinician. In industrial applications, non-fiber optic systems may be used.

The nozzle 71 is employed to create an engineered combination of small particles of the chosen fluid. The nozzle 71 may comprise several different designs including liquid only, air blast, air assist, swirl, solid cone, etc. When fluid exits the nozzle 71 at a given pressure and rate, it is transformed into particles of user-controllable sizes, velocities, and spatial distributions. The nozzle may have spherical, oval, or other shaped openings of any of a variety of different sizes, according to design parameters.

FIG. 5 illustrates a control panel 77 for allowing user-programmability of the atomized fluid particles. By changing the pressure and flow rates of the fluid, for example, the user can control the atomized fluid particle characteristics. These characteristics determine absorption efficiency of the laser energy, and the subsequent cutting effectiveness of the electromagnetically induced mechanical cutter. This control panel may comprise, for example, a fluid particle size control 78, a fluid particle velocity control 79, a cone angle control 80, an average power control 81, a repetition rate 82 and a fiber selector 83.

The cone angle may be controlled, for example, by changing the physical structure of the nozzle 71. Various nozzles 71 may be interchangeably placed on the electromagnetically induced mechanical cutter. Alternatively, the physical structure of a single nozzle 71 may be changed.

Figure 6:
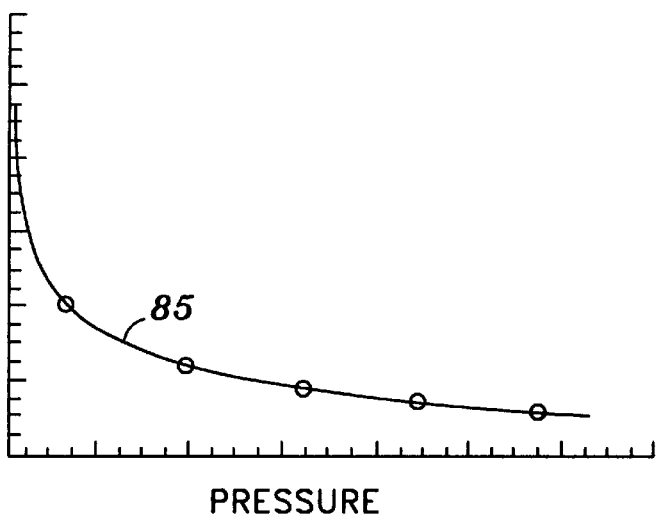
FIG. 6 is a plot of particle size versus fluid pressure.
Figure 7:
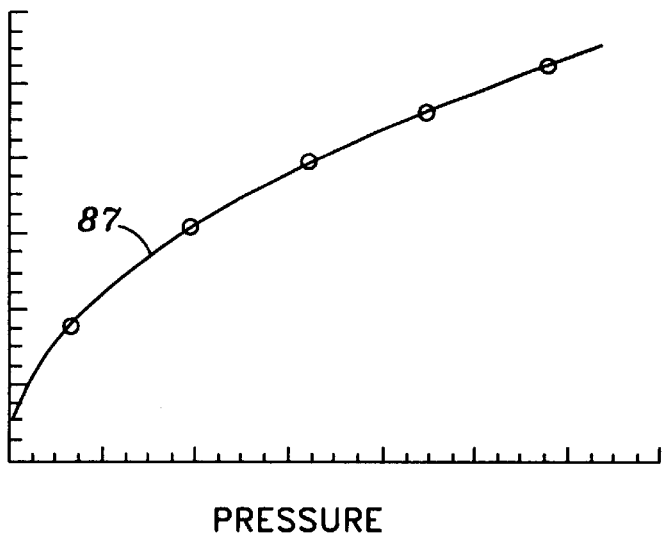
FIG. 7 is a plot of particle velocity versus fluid pressure.

FIG. 6 illustrates a plot 85 of mean fluid particle size versus pressure. According to this figure, when the pressure through the nozzle 71 is increased, the mean fluid particle size of the atomized fluid particles decreases. The plot 87 of FIG. 7 shows that the mean fluid particle velocity of these atomized fluid particles increases with increasing pressure.

According to the present invention, materials are removed from a target surface by mechanical cutting forces, instead of by conventional thermal cutting forces. Laser energy is used only to induce mechanical forces onto the targeted material. Thus, the atomized fluid particles act as the medium for transforming the electromagnetic energy of the laser into the mechanical energy required to achieve the mechanical cutting effect of the present invention. The laser energy itself is not directly absorbed by the targeted material. The mechanical interaction of the present invention is safer, faster, and eliminates the negative thermal side-effects typically associated with conventional laser cutting systems.

The fiber optic guide 23 (FIG. 4a) can be placed into close proximity of the target surface. This fiber optic guide 23, however, does not actually contact target surface. Since the atomized fluid particles from the nozzle 71 are placed into the interaction zone 59, the purpose of the fiber optic guide 23 is for placing laser energy into this interaction zone, as well. One feature of the present invention is the formation of the fiber optic guide 23 of straight or bent sapphire. Regardless of the composition of the fiber optic guide 23, however, another feature of the present invention is the cleaning effect of the air and water, from the nozzle 71, on the fiber optic guide 23.

The present inventors have found that this cleaning effect is optimal when the nozzle 71 is pointed somewhat directly at the target surface. For example, debris from the mechanical cutting are removed by the spray from the nozzle 71.

Figure 8:
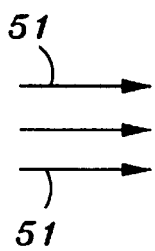
FIG. 8 is a schematic diagram illustrating a fluid particle, a source of electromagnetic energy, and a target surface according to the present invention.
Figure 8:
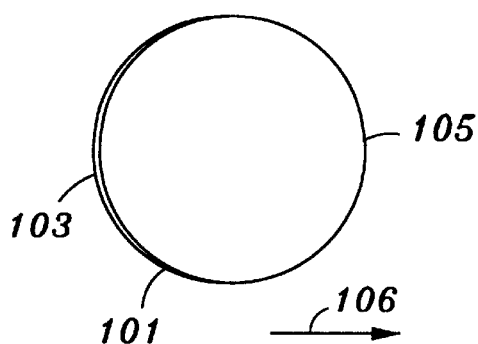
Figure 8:
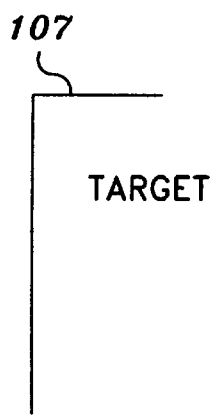

Additionally, the present inventors have found that this orientation of the nozzle 71, pointed toward the target surface, enhances the cutting efficiency of the present invention. Each atomized fluid particle contains a small amount of initial kinetic energy in the direction of the target surface. When electromagnetic energy from the fiber optic guide 23 contacts an atomized fluid particle, the exterior surface of the fluid particle acts as a focusing lens to focus the energy into the water particle's interior. As shown in FIG. 8, the water particle 101 has an illuminated side 103, a shaded side 105, and a particle velocity 106. The focused electromagnetic energy is absorbed by the water particle 101, causing the interior of the water particle to heat and explode rapidly. This exothermic explosion cools the remaining portions of the exploded water particle 101. The surrounding atomized fluid particles further enhance cooling of the portions of the exploded water particle 101. A pressure-wave is generated from this explosion. This pressure-wave, and the portions of the exploded water particle 101 of increased kinetic energy, are directed toward the target surface 107. The incident portions from the original exploded water particle 101, which are now traveling at high velocities with high kinetic energies, and the pressure-wave, impart strong, concentrated, mechanical forces onto the target surface 107.

These mechanical forces cause the target surface 107 to break apart from the material surface through a "chipping away" action. The target surface 107 does not undergo vaporization, disintegration, or charring. The chipping away process can be repeated by the present invention until the desired amount of material has been removed from the target surface 107. Unlike prior art systems, the present invention does not require a thin layer of fluid. In fact, it is preferred that a thin layer of fluid does not cover the target surface, since this insulation layer would interfere with the above-described interaction process.

The nozzle 71 is preferably configured to produce atomized sprays with a range of fluid particle sizes narrowly distributed about a mean value. The user input device for controlling cutting efficiency may comprise a simple pressure and flow rate gauge 75 (FIG. 4b) or may comprise a control panel as shown in FIG. 5, for example. Upon a user input for a high resolution cut, relatively small fluid particles are generated by the nozzle 71. Relatively large fluid particles are generated for a user input specifying a low resolution cut. A user input specifying a deep penetration cut causes the nozzle 71 to generate a relatively low density distribution of fluid particles, and a user input specifying a shallow penetration cut causes the nozzle 71 to generate a relatively high density distribution of fluid particles. If the user input device comprises the simple pressure and flow rate gauge 75 of FIG. 4b, then a relatively low density distribution of relatively small fluid particles can be generated in response to a user input specifying a high cutting efficiency. Similarly, a relatively high density distribution of relatively large fluid particles can be generated in response to a user input specifying a low cutting efficiency.

Soft tissues may include fat, skin, mucosa, gingiva, muscle, heart, live , kidney, brain, eye, and vessels, and hard tissue may include tooth enamel, tooth dent in, tooth cementum, tooth decay, amalgam, composites materials, tarter and calculus, bone, and cartilage. The term "fat" refers to animal tissue consisting of cells distended with greasy or oily matter. Other soft tissues such as breast tissue, lymphangiomas, and hemangiomas are also contemplated. The hard and soft tissues may comprise human tissue or other animal tissue. Other materials may include glass and semiconductor chip surfaces, for example. The electromagnetically induced mechanical cutting mechanism can be further be used to cut or ablate biological materials, ceramics, cements, polymers, porcelain, and implantable materials and devices including metals, ceramics, and polymers. The electromagnetically induced cutting mechanism can also be used to cut or ablate surfaces of metals, plastics, polymers, rubber, glass and crystalline materials, concrete, wood, cloth, paper, leather, plants, and other man-made and naturally occurring materials. Biological materials can include plaque, tartar, a biological layer or film of organic consistency, a smear layer, a polysaccharide layer, and a plaque layer. A smear layer may comprise fragmented biological material, including proteins, and may include living or decayed items, or combinations thereof A polysaccharide layer will often comprise a colloidal suspension of food residue and saliva. Plaque refers to a film including food and saliva, which often traps and harbors bacteria therein. These layers or films may be disposed on teeth, other biological surfaces, and nonbiological surfaces. Metals can include, for example, aluminum, copper, and iron.

A user may adjust the combination of atomized fluid particles exiting the nozzle 71 to efficiently implement cooling and cleaning of the fiber optic guide 23 (FIG. 4a), as well. According to the present invention, the combination of atomnized fluid particles may comprise a distribution, velocity, and mean diameter to effectively cool the fiber optic guide 23, while simultaneously keeping the fiber optic guide 23 clean of particular debris which may be introduced thereon by the surgical site.

Looking again at FIG. 8, electromagnetic energy contacts each atomized fluid particle 101 on its illuminated side 103 and penetrates the atomized fluid particle to a certain depth. The focused electromagnetic energy is absorbed by the fluid, inducing explosive vaporization of the atomized fluid particle 101.

The diameters of the atomized fluid particles can be less than, almost equal to, or greater than the wavelength of the incident electromagnetic energy. In each of these three cases, a different interaction occurs between the electromagnetic energy and the atomized fluid particle. When the atomized fluid particle diameter is less than the wavelength of the electromagnetic energy ($d<\lambda$), the complete volume of fluid inside of the fluid particle 101 absorbs the laser energy, inducing explosive vaporization. The fluid particle 101 explodes, ejecting its contents radially. As a result of this interaction, radial pressure-waves from the explosion are created and projected in the direction of propagation. The resulting portions from the explosion of the water particle 101, and the pressure-wave, produce the "chipping away" effect of cutting and removing of materials from the target surface 107. When the fluid particle 101 has a diameter, which is approximately equal to the wavelength of the electromagnetic energy ($d \approx \lambda$), the laser energy travels through the fluid particle 101 before becoming absorbed by the fluid therein. Once absorbed, the distal side (laser energy exit side) of the fluid particle heats up, and explosive vaporization occurs. In this case, internal particle fluid is violently ejected through the fluid particle's distal side, and moves rapidly with the explosive pressure-wave toward the target surface. The laser energy is able to penetrate the fluid particle 101 and to be absorbed within a depth close to the size of the particle's diameter. When the diameter of the fluid particle is larger than the wavelength of the electromagnetic energy (d>λ), the laser energy penetrates the fluid particle 101 only a small distance through the illuminated surface 103 and causes this illuminated surface 103 to vaporize. The vaporization of the illuminated surface 103 tends to propel the remaining portion of the fluid particle 101 toward the the targeted material surface 107. Thus, a portion of the mass of the initial fluid particle 101 is converted into kinetic energy, to thereby propel the remaining portion of the fluid particle 101 toward the target surface with a high kinetic energy. This high kinetic energy is additive to the initial kinetic energy of the fluid particle 101. The effects can be visualized as a micro-hydro rocket with a jet tail, which helps propel the particle with high velocity toward the target surface 107. The electromagnetically induced mechanical cutter of the present invention can generate a high resolution cut. Unlike the cut of the prior art, the cut of the present invention is clean and precise. Among other advantages, this cut provides an ideal bonding surface, is accurate, and does not stress remaining materials surrounding the cut.

Figure 9:
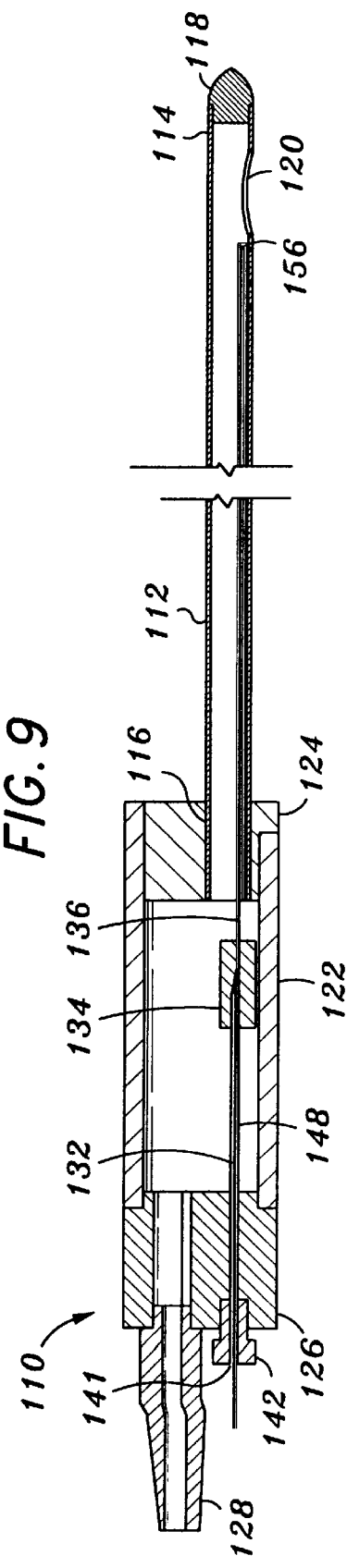
FIG. 9 is a side cut-away elevation view of a preferred non-thermal tissue remover of the present invention.
Figure 10:
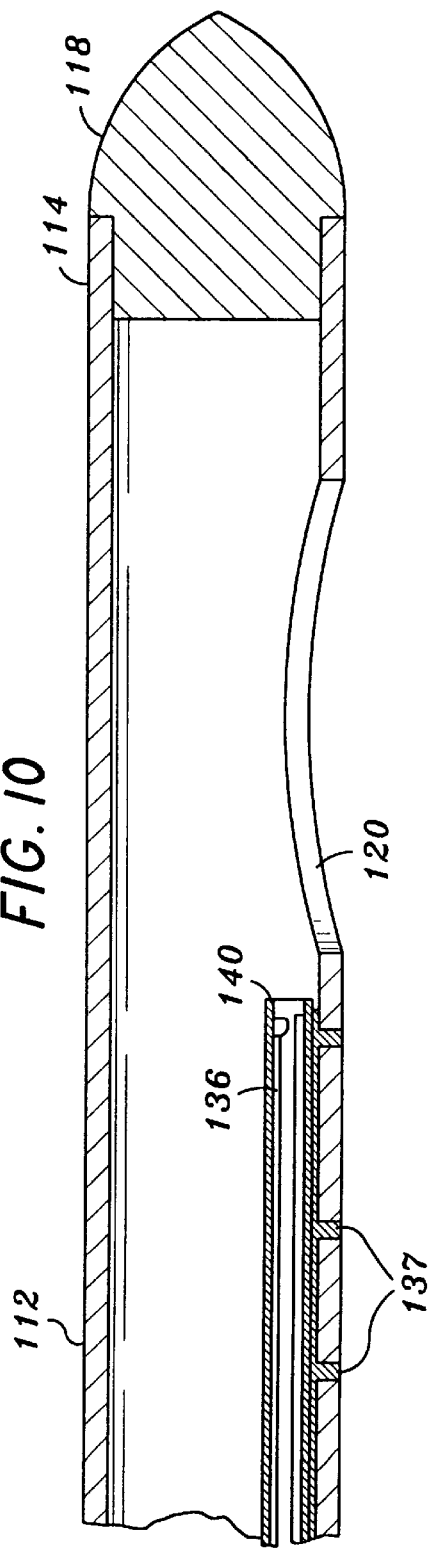
FIG. 10 is an exploded longitudinal section view of the distal end of the cannula.

FIGS. 9 and 14 illustrate a non-thermal tissue remover 110 which utilizes an electromagnetically induced mechanical cutter in accordance with the present invention. The non-thermal tissue remover 110 includes an aspiration cannula 112 having soft tissue aspiration inlet port 120 adjacent to the distal end 114 and cannula tip 118. As illustrated in FIGS. 9 and 10 the cannula tip 118 can advantageously be a generally rounded, blunt or bullet shaped tip attached to the cannula 112 by welding or soldering. As illustrated in FIG. 9, the cannula proximal end 116 is retaine within the distal handle end cap 124, the aspirated soft tissue outlet port 128 is retaine within the proximal handle end cap 126, and the distal handle end cap 124 and proximal handle end cap 126 are retained within the handle 122. The soft tissue outlet port 128 is connected to an aspiration source by a plastic tubing (not shown).

As illustrated in FIGS. 9–13, a fluid and laser fiber guide tube extends longitudinally within the non-thermal tissue remover 110 from the proximal handle end cap 126, at the laser and fluid source port 141, terminating at a point 140 (FIG. 10) immediately proximal to the soft tissue aspiration inlet port 120. The fluid and laser fiber guide tube 136 resides partially within a coaxial fluid channel 130 (FIG. 12) drilled in the proximal handle end cap 126, and comprises a large fluid and laser fiber guide tube 132, a guide tube transition coupler 134, and a small fluid and laser fiber guide tube 136. The guide tube transition coupler 134 is positioned within the handle 122 proximal to the proximal end of the cannula 116 and is drilled to accommodate the external diameters of the large 132 and small guide tubes 136 . The guide tube components are joined together and to the proximal handle end cap 126 and within the aspiration cannula inner wall utilizing a means such as soldering or welding. The fluid and laser guide tube can be provided with an O-ring seal 146 (FIG. 12) at its retention within the proximal handle end cap 126 at the laser energy source port 141. The optional guide tube transition coupler 134 can be used to provide for a small fluid and laser fiber guide tube 136 having a relatively small diameter. The optional guide tube transition coupler 134 also allows for more space within the aspiration cannula 112.

Figure 11:
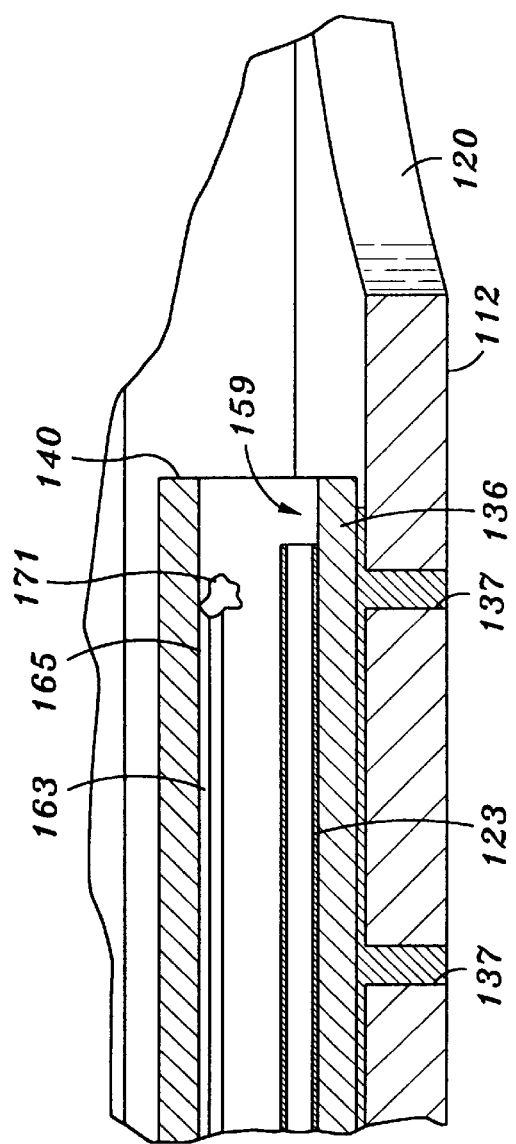
FIG. 11 is an exploded view similar to FIG. 10, showing an electromagnetically induced mechanical cutter disposed adjacent the soft tissue aspiration inlet port.
Figure 12:
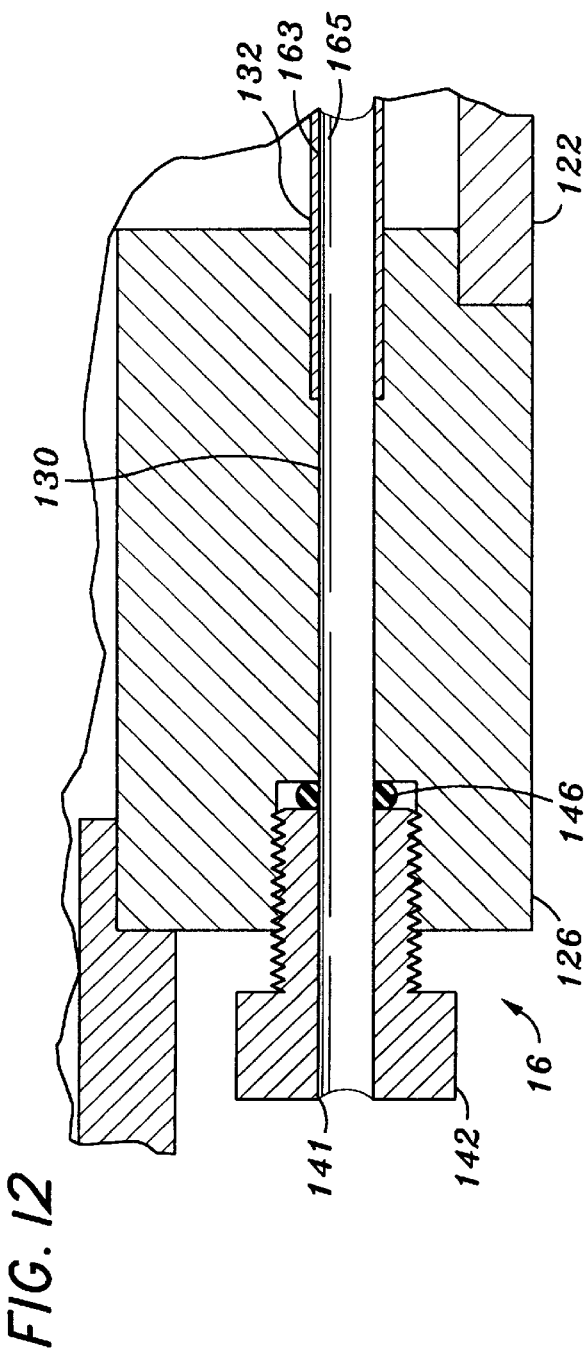
FIG. 12 is a partial exploded longitudinal section view of the handle and proximal end cap showing the laser fiber and sources of fluids within the fluid and laser guide tube.
Figure 13:
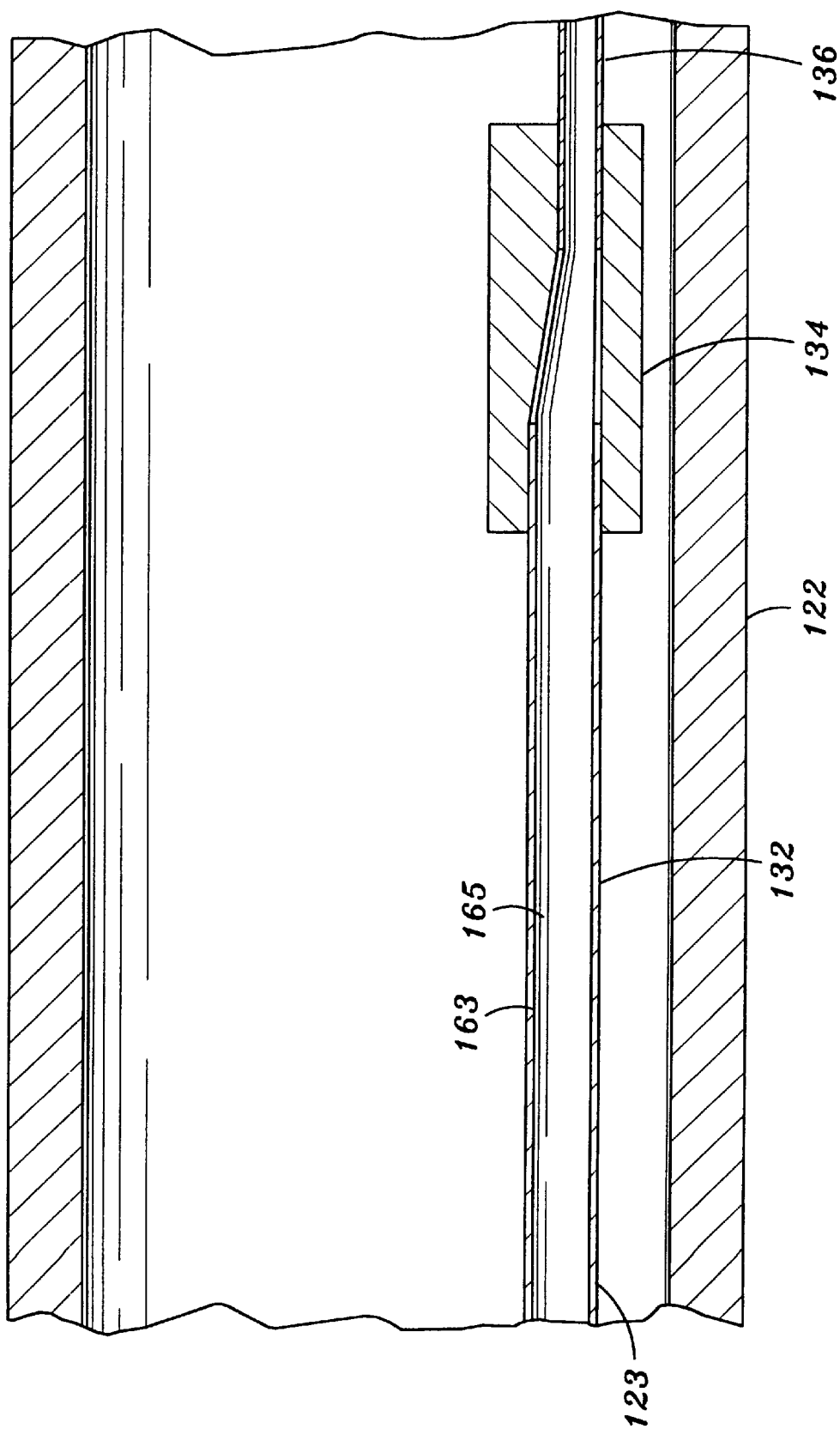
FIG. 13 is a partial exploded longitudinal section of a guide tube transmission coupler positioned within the handle.

Housed within the fluid and laser fiber guide tube is the laser fiber optic delivery system. As shown in FIG. 11, the laser fiber optic delivery system comprises a fiber optic guide 123, an air tube 163 and a water tube 165. The fiber optic guide 123, air tube 163 and water tube 165 are preferably similar to the fiber optic guide 23, air tube 63 and water tube 65 described above with reference to FIG. 4a. The water tube 165 is preferably connected to a saline fluid source and pump, and the air tube is preferably connected to a pressurized source of air. The air tube 163 and the water tube 165 are terminated with a nozzle 171 which is preferably similar to the nozzle 71 described above with reference to FIG. 4a. In one embodiment, the fiber optic guide 123, air tube 163, and water tube 165 operate together to generate electromagnetically induced mechanical cutting forces. Any of the above-described configurations may be implemented to generate such forces, in modified embodiments.

In the presently preferred embodiment wherein the fluid emitted from the water tube is water-based and the electromagnetic energy from the fiber optic guide 123 is highly absorbed by the water, it is desirable to have a relatively non-aqueous environment (wherein body fluids are minimized) between the output end of the fiber optic guide 123 and the target surface. It is also preferred to maintain a non-aqueous environment between the nozzle 71 and the interaction zone 159 (FIG. 11) for generation of the atomized distributions of fluid particles. An element of the present invention involves keeping body fluids clear from the nozzle 71 and the interaction zone 159 to enhance performance. Accordingly, means for reducing bleeding, for example, are preferred. In this connection, the distal blade of the cannula tip 118 can comprise a radio frequency (RF) cutting wire. Electrosurgery procedures using RF cutting wires implement high frequency (radio frequency) energy for implementing cutting of soft tissue and various forms of coagulation.

In electrosurgery, the high density of the RF current applied by the active electrosurgical electrode causes a cutting action, provided the electrode has a small surface (wire, needle, lancet, scalpel). Additionally, the current waveform is a significant factor in the cutting performance. A smooth, non-modulated current is more suitable for scalpel-like cutting, whereas the modulated current provides cuts with predetermined coagulation. The output intensity selected, as well as the output impedance of the generator, are also important with respect to cutting performance. The electrosurgical cutting electrode can comprise a fine microneedle, a lancet, or a knife, and preferably comprises a wire or band loop. Depending on (1) the shape of the electrode, (2) the frequency and wave modulation, (3) the peak-to-peak voltage, and (4) the current and output impedance of the generator, the cut can be smooth, with absolutely no arcing, or it can be charring and burn the tissue. Electrosurgical coagulation may be carried out, for example, by implementing light charring and burning in a spray coagulation mode. The biological effect, accordingly, can significantly differ from gentle tissue dehydration to burning, charring and even carbonization. The temperature differences during the various coagulation procedures can vary between 100 degrees Celsius to well over 500 degrees Celsius. The means should be chosen in accordance with the amount of cutting and/or coagulation that is desired, which will be a function of various parameters such as the type of tissue being cut. In accordance with an object of the present invention of reducing smoke, bipolar applications or cutting with no-modulated current are preferred.

Pressurized air can be output from the air tube 163 at various flow rates and various intervals, either during cutting or between cutting, in order to provide a relatively non-aqueous working environment for the electromagnetically induced mechanical cutting forces. The application of air should be controlled to prevent any possibility of embolisms being introduced into the patient's bloodstream. Insufflation procedures, for example, for generating air cavities in the vicinity of the target tissue to be cut and removed can be used to attenuate the introduction of unwanted body liquids in the interaction zone 159.

In accordance with the presently preferred embodiment, the negative pressure generated and transmitted by the flexible suction tubing serves to evacuate from the interaction zone 159 body fluids, removed tissue, and air and water. As presently embodied, the large fluid and laser fiber guide tube 132 is connected to a controlled source of air and the negative pressure generated and transmitted by the flexible suction tubing serves to draw the air through the large fluid and laser fiber guide tube 132 and the small fluid and laser fiber guide tube 136. The source of air couple to the large fluid and laser fiber guide tube 132 preferably comprises moist air. The flow of air out of the small fluid and laser fiber guide tube 136 serves to keep the nozzle 171, the output end 140 of the fiber optic guide 123, and the interaction zone 159 relatively free of body fluids. The rate of air drawn should be relatively low in environments where embolisms may be formed.

If additional removal of body fluids is desired, one or more pressurized air lines can be routed to distal end 114 of the cannula 114 adjacent to the cannula tip 118. The pressurized air line or lines can be activated to introduce air into the lumen of the cannula at the distal end of the cannula to thereby facilitate the removal of body fluids and water from the lumen. Effective removal of body fluids and water from the distal end of the cannula, including the interaction zone 159 and the portion of the lumen distal of the aspiration inlet port, occurs when fatty tissue within the aspiration inlet port forms a seal around the aspiration inlet port so that body fluids are drawn out of the cannula lumen by the negative pressure. The pressurized air line or lines provide displacement (preferably at a relatively low flow rate if any risk of embolism generation is present) for the fluids as they are removed. If the body fluids are viscous then water (with or without additives) from the water tube 165 can be introduced to attenuate the viscosity of and accelerate the removal of the body fluids.

In accordance with the presently preferred embodiment only water is delivered to the nozzle 171 during cutting. One or more controls disposed proximally of the aspirated soft tissue outlet port 128 can allow the user to adjust the percent of air and/or water that is directed to the nozzle 171 at any given time. In the presently preferred embodiment a control panel, having one or more of the features of the control panel 77 shown in FIG. 5, is used to control, among other things, whether water alone, air alone, or a combination of air and water is supplied to the nozzle 171.

The large guide tube 132 is maintained in position within cannula 112, for example, by silver solder through holes 137, as illustrated in FIGS. 10 and 11. The retention of the laser fiber optic delivery system is accomplished by a retaining screw 142 at the fluid, air and laser energy source port 141. As will be apparent to those skilled in this art, a shorter and thinner soft tissue aspiration cannula 112 will be useful in more restricted areas of the body, as under the chin, and a longer and larger diameter cannula will be useful in areas such as the thighs and buttocks where the cannula may be extended into soft tissue over a more extensive area.

To perform the method of the present invention as illustrated in FIG. 14, the surgeon determines the location and extent of soft tissue to be removed. The appropriate size non-thermal tissue remover 110 is selected. A short incision is made and the cannula tip 118 and the distal end of the cannula 114 are passed into the soft tissue to be removed. Saline is delivered through the water tube 165. The aspiration pump is then activated. The resultant negative pressure thus generated is transmitted to the non-thermal tissue remover 110 via a flexible suction tubing, to the soft tissue outlet port 128, through the handle 122, through the cannula 112, to the soft tissue aspiration inlet port 120. The resultant negative pressure at the inlet port draws a small portion of the soft tissue into the lumen of the cannula 112, into close proximity with the interaction zone 159 (FIG. 11). While the negative pressure is maintained, a controlled flow of air is fed through the large and small fluid and laser fiber guides and into the lumen of the cannula. The laser is then activated and electromagnetically induced mechanical cutting forces are imparted onto the soft tissue within the cannula lumen, cleaving the soft tissue. Additional soft tissue enters the soft tissue aspiration inlet port 120 by virtue of a reciprocating longitudinal motion of the non-thermal tissue remover 110 within the soft tissue. This reciprocating motion is applied by the surgeon's hand on the handle 122. The reciprocating motion of the non-thermal tissue remover 110, with respect to the surrounding soft tissue, is facilitated by the stabilization of the soft tissue by the surgeon's other hand placed on the skin overlying the cannula soft tissue aspiration inlet port 120. Soft tissue is removed from the vicinity of the inlet port 120 to the more proximal portion of the lumen of the cannula, and eventually out the cannula to the soft tissue outlet port 128 by the negative pressure generated by the aspiration pump.

The soft tissue aspiration cannula 112, cannula tip 118, handle 122, distal handle end cap 124, proximal handle end cap 126, aspirated soft tissue outlet port 128, large fluid and laser fiber guide tube 132, guide transition coupler 134, small fluid and laser fiber guide tube 136, and retaining screw 142 are all preferably of stainless steel. As will be apparent to those of skill in this art, a shorter and thinner diameter aspiration cannula will be useful in more restricted areas of the body, as around small appendages, and a longer and larger diameter cannula will be useful in areas, such as the thighs and buttocks, where the cannula may be extended into fatty tissue over a more extensive area. The cannula tip 118 is in sizes of the same diameter as the aspiration cannula O.D., machined to a blunt tip and to fit the cannula inside diameter. The handle 122 is preferably of tubing. The distal handle end cap 124 is preferably machined to fit the handle inside diameter and drilled to accommodate the aspiration cannula outside diameter. The proximal handle end cap 126 is preferably machined to fit the handle inside diameter, drilled to accommodate the aspiration outlet port, fluid and laser guide channel, and large guide tube, and drilled and tapped to accommodate the retaining screw. The aspirated soft tissue outlet port 128 is preferably machined to fit the proximal handle end cap and tapered to accommodate appropriate suction tubing. The guide tube transition coupler 134 is preferably drilled to accommodate large and small guide tubes 132 and 136. The small fluid and laser fiber guide tube is determined by the length of the cannula 112.

By utilizing the present non-thermal tissue remover 110 according to the present method, a variety of advantages are achieved. By enabling the cutting of the soft tissue in a straight line, the scooping, ripping and tearing action characteristic of prior-art devices, is attenuated, resulting in fewer contour irregularities and enhanced satisfaction. With the addition of the cutting action of the present invention the rate of removal of unwanted soft tissue can be enhanced over that of previous devices and techniques thus decreasing operative time. Benefits are obtained without fear of peripheral laser thermal damage.

In accordance with the present invention, water from the water tube 165 can be conditioned with various additives. These additives may include procoagulants and anesthetics, for example. Other additives may be used, such as other medications. Co-pending U.S. application Ser. No. 08/995,241 filed on Dec. 17, 1997 and entitled FLUID CONDITIONING SYSTEM, which is a continuation of U.S. application Ser. No. 08/575,775, filed on Dec. 20, 1995 and entitled FLUID CONDITIONING SYSTEM which issued into U.S. Pat. No. 5,785,521, discloses various types of conditioned fluids that can be used with the electromagnetically induced mechanical cutter of the present invention in the context of non-thermal soft tissue removal. Other additives can include solubilizing and emulsifying agents in modified embodiments when an object to be pursued is to solubilize and emulsify the fatty tissue being removed. All of the additives should preferably be biocompatible.

Although an exemplary embodiment of the invention has been shown and described, many changes, modifications and substitutions may be made by one having ordinary skill in the art without necessarily departing from the spirit and scope of this invention.

What is claimed is:

1. An in vivo surgical method of aspirating soft tissue from a patient comprising:

inserting an aspiration cannula through the patient's epidermis, so that a distal end of the cannula is positioned in an area of soft tissue and a portion of the area of soft tissue is within an aspiration inlet port, the cannula being provided with a central lumen in communication with the aspiration inlet port adjacent the cannula distal end;

transmitting air and fluid through a fluid and energy guide, the fluid and energy guide longitudinally extending within the central lumen;

generating atomized fluid particles in an interaction zone located in close proximity to the aspiration inlet port, using the air and fluid transmitted through the fluid and energy guide;

providing electromagnetic energy from an energy source to an electromagnetic energy transmitting means operatively mounted within the fluid and energy guide;

transmitting the electromagnetic energy from an output end of the electromagnetic energy transmitting means into the interaction zone, the electromagnetic energy having a wavelength which is substantially absorbed by a portion of atomized fluid particles in the interaction zone, the absorption of the electromagnetic energy by the portion of atomized fluid particles causing the portion of atomized fluid particles to expand and impart disruptive mechanical cutting forces onto the portion of the area of soft tissue within the aspiration inlet port; and providing a source of aspiration at a proximal end of the cannula to aspirate soft tissue through said aspiration inlet port and the cannula.

2. The method of claim 1, wherein the soft tissue is fatty tissue between the patient's epidermis and muscle.

3. The method of claim 1, wherein the soft tissue is located within the brain, the eye, the trachea or the abdomen.

4. The method of claim 1, wherein the cannula distal end is generally rounded or bullet-shaped to facilitate insertion into the patient's tissue with a minimum of localized tissue trauma.

5. The method of claim 1, wherein the electromagnetic energy source comprises an erbium, chromium, yttrium, scandium, gallium garnet (Er, Cr:YSGG) solid state laser.

6. The method of claim 1, wherein the electromagnetic energy transmitting means comprises a fiber optic guide.

7. The method of claim 1, wherein the fluid comprises water.

8. A tissue remover comprising:

an aspiration cannula having a cannula proximal end and a cannula distal end, the aspiration cannula having an aspiration inlet port at the distal end and being provided with a central lumen in communication with the aspiration inlet port adjacent the cannula distal end, the aspiration inlet port being adapted to receive soft tissue therein and into the central lumen;

a fluid and energy guide disposed within the aspiration cannula and longitudinally extending within the central lumen, the fluid and energy guide transporting air and fluid to a distal end of the fluid and energy guide and being adapted to generate atomized fluid particles in an interaction zone located in close proximity to the distal end of the fluid and energy guide near the aspiration inlet port, the fluid and energy guide further providing electromagnetic energy from an energy source to an electromagnetic energy transmitting means operatively mounted within the fluid and energy guide, the electromagnetic energy having a wavelength which is substantially absorbed by a portion of the atomized fluid particles in the interaction zone, the absorption of the electromagnetic energy by the portion of the atomized fluid particles causing the portion of the atomized fluid particles to expand and impart disruptive mechanical cutting forces onto the soft tissue within the aspiration inlet port; and a source of aspiration connected to a proximal end of the cannula, the source of aspiration being adapted to aspirate soft tissue through the aspiration inlet port and the cannula.

9. The tissue remover according to claim 8, wherein the electromagnetic energy source comprises an erbium, chromium, yttrium, scandium, gallium garnet (Er, Cr:YSGG) solid state laser.

10. The tissue remover according to claim 8, wherein the aspiration cannula is formed of stainless steel and is formed with a generally rounded or bullet-shaped distal end.

11. The tissue remover according to claim 8, wherein the electromagnetic energy transmitting means is a fiber optic delivery system.

12. The tissue remover as set forth in claim 8, wherein the atomized fluid particles generated by the fluid and energy guide comprise a substance for reducing bleeding.

13. The tissue remover as set forth in claim 8, wherein the atomized fluid particles generated by the fluid and energy guide comprise saline.

14. The tissue remover as set forth in claim 8, wherein the atomized fluid particles generated by the fluid and energy guide comprise an anesthetic.

* * * * *